United States Patent [19]

Haase

[11] Patent Number: 4,507,955
[45] Date of Patent: Apr. 2, 1985

[54] PIPETTE FOR CARRYING OUT AND DETERMINING SEDIMENTATION RATES, IN PARTICULAR THAT OF BLOOD

[76] Inventor: Walter Haase, Gelliehäuser Strasse 6, D-3407 Gleichen-Benniehausen, Fed. Rep. of Germany

[21] Appl. No.: 491,272

[22] Filed: May 4, 1983

[30] Foreign Application Priority Data

May 7, 1982 [DE] Fed. Rep. of Germany ....... 3217123

[51] Int. Cl.$^3$ ............................................. G01N 15/04
[52] U.S. Cl. .................................... 73/61.4; 73/864.01
[58] Field of Search .................. 73/61.4, 61 R, 864.01

[56] References Cited

U.S. PATENT DOCUMENTS 2,729,971  1/1956  Stein ................................. 73/61 R
3,864,979  2/1975  Ayres .

FOREIGN PATENT DOCUMENTS 2556801  6/1977  Fed. Rep. of Germany ....... 73/61.4
2631291  1/1978  Fed. Rep. of Germany .
2757039  6/1979  Fed. Rep. of Germany .

Primary Examiner—S. Clement Swisher
Assistant Examiner—Joseph W. Roskos
Attorney, Agent, or Firm—Thomas & Kennedy

[57] ABSTRACT

A pipette for carrying out and determining sedimentation rates, in particular that of blood sedimentation, comprises an ungraduated transparent tube (1) of glass, plastic or the like, at the lower end of which a filling connection (2) is provided which, with the aid of a tube-holder branch (4), sealingly retains the tube (1). The filling connection (2) comprises a filling branch (5) for attaching a syringe which contains the sedimentation material. In order to enable the sedimentation material to be filled in without bubbles, the axes of the tube-holder branch (4) and of the filling branch (5) mutually enclose an acute angle—especially of the order of magnitude of 30°—and no cross-section-constricting inserts which would impair the free cross-section of the channel (6) are provided in the filling connection (2).

7 Claims, 1 Drawing Figure

U.S. Patent  Apr. 2, 1985  4,507,955
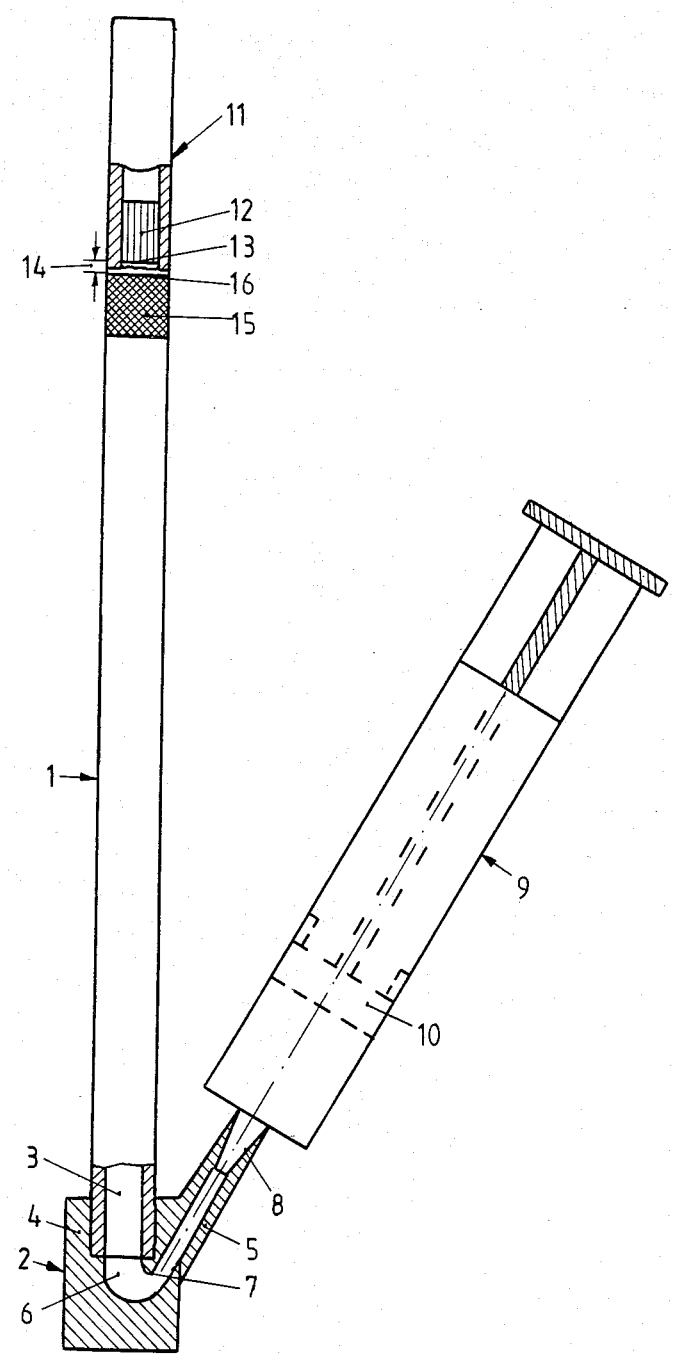

PIPETTE FOR CARRYING OUT AND DETERMINING SEDIMENTATION RATES, IN PARTICULAR THAT OF BLOOD

The invention relates to a pipette for carrying out and determining sedimentation rates, in particular that of blood sedimentation, using a transparent tube, in particular an ungraduated tube, of glass, plastic or the like, to the lower end of which, via a tube-holder branch, a filling connection can be attached which has a filling branch for attaching a syringe containing the sedimentation material. The filling connection can also have been attached to the tube beforehand, by pushing the tube sealingly into the tube-holder branch.

A pipette of this type has been disclosed by German Utility Model No. 77 37,145. The filling branch encloses an angle of 90° with the tube-holder branch. The filling branch is intended for attaching the blood collection syringe. The essential point is that a restrictor in the form of a double check valve is provided in the filling connection. If, with this pipette, the blood is filled in while the tube is upright, it cannot be excluded that air bubbles pass from the filling connection and/or the blood collection syringe into the column of blood rising in the tube and thus can cause false measurements. Due to the restrictor in the form of a double check valve, acting at the lower end of the tube, a considerable flow constriction is created, so that the injection of the blood through this restrictor orifice entails high flow velocities, so that a considerable turbulence of the blood with the air present in the colume arises, it also being possible for foam to be formed. When the syringe is tightly placed against the filling branch, a largely closed volume of air is blocked in between the connection point and the restrictor, the sedimentation material being ejected into this air volume. Mixing and bubble formation cannot be prevented in this way.

Furthermore, pipettes are known in which, on a transparent tube, a filling connection is provided which is aligned with the tube axis and is arranged to be rotatable and at the same time to act as an isolation valve. It is known that, in order to fill the sedimentation material without bubbles, the syring containing the sedementation material can be attached obliquely downwards, so that air bubbles contained in the collection syringe cannot be ejected at the same time. In this case, however, graduated tubes are employed which are comparatively more expensive to manufacture.

Instead of using a rotary valve aligned in the axis of the tube, it also known to employ a ball valve in conjunction with a filling connection, in which case the ball comprising a part of the connecting line of the filling connection is mounted in the filling connection to be pivotable via the syringe. Since the connecting line through the ball runs in an acute angle, it is possible in this case to empty the syringe obliquely downwards with the tube upright in the filling position, the axis of the syringe and the axis of the tube enclosing approximately a mutual angle of 60°. After the filling procedure, the ball is rotated in such a way that the syringe comes to lie approximately horizontally, that is to say it projects from the tube at an angle of 90°. This pipette is also very expensive. Moreover, sharp edges and inserts which restrict the flow act in the line through the filling connection. For example, the line has a smaller diameter than that corresponding to the internal diameter of the tube. On filling, an increased flow velocity necessarily results in the zone of the filling connection, and hence also vigorous mixing and turbulence with the enclosed air.

It is the object of the invention to provide a pipette of the type described at the outset, by means of which it is possible, on the one hand, for the sedimentation material to be filled in without bubbles and, on the other hand, to manage without a check valve, isolation valve or the like, so that disposable pipettes of this type can be manufactured at particularly low cost.

According to the invention, this is achieved when the axes of the tube-holder branch and of the filling branch mutually enclose an acute angle, preferably 30°, and when the filling connection does not have any inserts, constricting the cross-section, in its free cross-section. In this way, it is possible, with the tube approximately upright, to attach the syringe, pointing downwards, sealingly to the filling branch, so that air bubbles which may be present in the syringe cannot be forced during filling into the tube zone. On the other hand, anything which could adversely affect the flow should be avoided in the passage through the filling connection and at the transition between the tube-holder branch and the tube. There is neither a restrictor valve nor an isolation valve. The cross-section at this point is not constricted, so that increased flow velocities during filling also do not arise. This ensures that, when the syringe is sealingly attached to the filling branch, the air enclosed in the filling connection is pushed through the tube in front of the sedimentation material supplied at uniform velocity, so that no turbulence of this air with the sedimentation material occurs. It is to be understood that the syringe remains on the filling branch during the sedimentation process so that, in the end position of the pressed-down piston of the syringe, a counter-pressure corresponding to the pressure acting on the surface of the column of sedimentation material in the tube is obtained. Initially, this suffices for isolating the column of blood. During the sedimentation, the sediment settles at the lowermost point, that is to say in the filling connection, the sediment itself forming the closure of the column. This replaces the use of an isolation value in an adroit manner.

In particular, the tube and the tube-holder branch on the filling connection have the same internal diameter; rounded edges can be provided at the transition from the filling branch to the tube-holder branch, in order to avoid locally increased flow velocities at this point.

In order to enable the sedimentation material to be filled in not only without bubbles but also without a meniscus, a filter insert designed to be permeable to water and air can be provided on the end zone of the tube, remote from the filling connection. It is to be understood that this filter insert is provided in the cross-section of the tube near to one end, that is to say it was introduced and fitted there during manufacture. With such a filter insert, it is possible to end the filling step when the surface of the column of the sedimentation material comes into contact with the underside of the filter insert, so that the curved meniscus disappears and a horizontal zero marking or a reference point for the height of the column results. Such a filter insert thus guarantees always identical initial conditions and hence considerably facilitates filling. Air which has been pushed forward during filling in front of the sedimentation material can escape through the filter insert. The result of the combination of the inclined filling branch with the filter insert in that it is possible, and ensured, that the sedimentation material is filled in without bubbles and without a meniscus and with an absolute boundary. Thus, an unambiguous reference point for the start of the sedimentation process is set.

When the blood is used as the sedimentation material the filter insert can have a porosity of 1 to 10μ—especially 5μ. Plastic filters have proved to be particularly suitable for this purpose.

In a further development of the invention, an absorbent body can be provided, between the filter insert in the tube and the filling connection, at a spacing from the lower edge of the filter insert. As a result, the pipette can be used for an automatic evaluation of the sedimentation rate. With particular advantage, it can be employed in the case of electronic evaluation according to German Patent Specification No. 2,757,039, because the absorbent body causes the signal to be switched off or, due to the spacing between the lower end of the filter insert and the upper end of the absorbent body, a clearly defined length is set, over which the sedimentation rate can be monitored, the absorbent body supplying a clear end signal when the sedimentation limit reaches, and passes through, the upper boundary of the absorbent body. From this point in time, there is then no further change in the measuring range. The spacing between the absorbent body and the filter insert can be maintained or set within relatively narrow tolerances during manufacture, so that the length is known. It is, however, also possible to check this length one more during the automatic evaluation or in fact to measure it in order to produce the reference point. The spacing can be about 0.5 mm. The absorbent body can be provided on the outside or in the tube, or also in the material of the tube, for example it can be fused in. The way in which it is fitted depends on the manufacturing process which is most simple in the particular case.

An illustrative embodiment of the invention is represented in the drawing which shows a section through the pipette.

The pipette is composed of a tube 1 and a filling connection 2 as its essential constitutents. The two parts are manufactured separately from one another and can either be joined together, that is to say fitted into each other, by the manufacturer, or they can be sold separately so that they are fitted into each other only shortly before use. The tube 1 consists, for example, of glass, plastic or the like and is thus transparent in order to enable the sedimentation rate to be determined or observed. The tube 1 has a continuous constant internal diameter 3 over its length.

The filling connection 2 comprises a tube-holder branch 4 and a filling branch 5, which are mutually connected in the filling connection 2 via a channel 6. At least in its part located in the tube-holder branch 4, the channel 6 has an internal diameter which corresponds to the internal diameter 3 of the tube 1, so that a transition of the cross-section without flow-constricting inserts or the like is ensured here. Sharp edges, projections and the like in the channel 6 are also avoided, in particular at a transfer point 7 of the channel 6 from the filling branch 5 into the tube-holder branch 4. At the free end of the filling branch 5, a conical fitting face 8 is formed for a syringe 9 which contains the sedimentation material which, with the air of a piston 10, can be forced out of the syringe 9 in the known manner and filled into the tube 1. The essential point is that an acute angle is provided between the tube 1 or tube-holder branch 4 and the filling branch 5. The axes of the tube and of the filling branch or syringe 9 can here enclose a mutual angle of 30°.

This ensures that the sedimentation material can be filled without bubbles into the tube 1. When the syringe is filled in a position inclined downwards, bubbles contained in the syringe 9 collect at the upper end of the chamber of the syringe. The air, enclosed in the filling connection 2 due to the attachment of the syringe 9 to the conical fitting face 8, is pushed forward by and in front of the sedimentation material ejected from the syringe and rises in front of the sedimentation material in the tube 1. The fact that restrictors, isolation valves and other flow-constricting inserts in the filling connection 2 have been avoided makes it possible to push the air out in this way. With uniform pressure on the syringe 9, the flow velocity does not change while the sedimentation material is being filled in. The sedimentation material is thus filled in gently and without significant turbulence.

To enable the sedimentation material to be filled into the tube 1 not only without bubbles, but also without a meniscus and up to a defined height in each case, a filter insert 12, for example a plastic filter, is fitted in the upper end zone 11 of the tube 1 and arranged in a fixed position. The filter insert 12 is permeable to gas and water, but has only limited permeability for the sedimentation material, so that it is possible, even without particular skill, to fill the tube with sedimentation material up to the lower boundary 13 of the filter insert 12 which is of plane shape, so that the meniscus, which is usually present without such a filter insert, that is to say the doming of the upper boundary of the column of sedimentation material, disappears. This provides unambiguous and defined initial conditions for the sedimentation rate.

In a further development of the pipette, in particular for use with automatic evaluation of the sedimentation rate, an absorbent body 15 can be arranged in a fixed position below the filter insert 12 at a spacing 14. The absorbent body can be provided either in the tube 1, on the outer wall of the tube 1 or even in the wall of the tube 1. For example, it can consist of a coating applied to the outside or in any case of a material which is impervious to the evaluation signal. This unambiguously predetermines and sets the spacing 14 as a length for the sedimentation rate. Automatic evaluation is thus considerably facilitated. The measuring step is simplified, particularly in the case of electronic detection. in fact, when the sedimentation boundary has passed through the spacing 14 and reaches the zone of the absorbent body 15, there is no further change in the measuring length, that is to say the spacing 14, so that, because the measured signal remains constant, the disappearance of the sedimentation boundary in the zone of the absorbent body 15 can be detected very accurately. The spacing 14 can be about 0.5 mm or more. It is possible to maintain this spacing 14 very accurately even during manufacture, or to make less stringent demands on the accuracy, if the measuring instrument comprises a measuring device for first measuring this height of the spacing in each individual measurement case and for basing the measurement thereon. The upper boundary 16 of the absorbent body defines the spacing 14 from the boundary 13 of the filter insert 12. The axial length of the absorbent body 15 is not significant. Merely, it should be of such a magnitude that the measuring range is bounded by the filter insert 12 and the absorbent body 15.

I claim:

1. A pipette for carrying out and determining sedimentation processes, in particular blood sedimentation, including a normally upright transparent tube including at its lower end portion means for receiving a syringe containing the material to be introduced and sedimented, said tube having inside, in the region of its upper end, a filter insert, characterized in that, for filing the tube without a meniscus, said filter is permeable to gas and to the liquid in the material to be sedimented, said filter insert substantially filling the entire free cross-sectional area of the tube.

2. A pipette according to claim 1, characterised in that when the material to be sedimented is blood, the filter insert has a porosity of 1–10$\mu$, in particular 5$\mu$.

3. A pipette according to claim 2, characterised in that said means for receiving a syringe is provided on the lower end of the tube and has no components in its cross-section which constrict its cross-sectional area.

4. A pipette according to claim 3, characterised in that the internal passages of said tube and said means for receiving a syringe are joined with the same internal diameter, and said means for receiving the syringe includes a filling branch extending at an acute angle with respect to said tube, and said filling branch is joined to said tube with a rounded internal passage.

5. A pipette according to claim 2, characterised in that an absorbing element is provided between the filter insert in the tube and the means for receiving a syringe at a distance from the lower portion of the filter insert.

6. A pipette according to claim 5, characterised in that the distance is about 0.5 mm.

7. A pipette according to claim 5, characterised in that the absorbing element is located outside the tube.

* * * * *